United States Patent [19]
Sugi et al.

[11] Patent Number: 5,959,143
[45] Date of Patent: Sep. 28, 1999

[54] CATALYSTS AND PROCESS FOR THE PREPARATION THEREOF

[75] Inventors: Hideki Sugi, Tamamura-machi; Fumio Sakai, Gunma-machi; Koichi Wada, Yamato; Kazuo Shiraishi, Annaka; Toshitake Kojima; Atsushi Umejima, both of Tamamura-machi; Yoshimasa Seo, Yamaguchi-ken, all of Japan

[73] Assignee: Nippon Kayaku Kabushiki Kaisha, Tokyo, Japan

[21] Appl. No.: 08/737,028

[22] PCT Filed: Mar. 1, 1996

[86] PCT No.: PCT/JP96/00506

§ 371 Date: Oct. 30, 1996

§ 102(e) Date: Oct. 30, 1996

[87] PCT Pub. No.: WO96/27437

PCT Pub. Date: Sep. 12, 1996

[30] Foreign Application Priority Data

Mar. 3, 1995 [JP] Japan .................................... 7-068951
Feb. 27, 1996 [JP] Japan .................................... 8-063947

[51] Int. Cl.$^6$ .......................... C07C 51/235; B01J 23/22
[52] U.S. Cl. .......................... 562/534; 502/302; 502/304; 502/305; 502/306; 502/307; 502/308; 502/309; 502/310; 502/312; 562/535
[58] Field of Search ................... 502/311, 247, 502/249, 306, 309, 212, 213, 312, 302, 304, 305, 307, 308, 310; 562/534, 535

[56] References Cited

U.S. PATENT DOCUMENTS

| 4,014,925 | 3/1977 | Ferlazzo et al. | 502/312 |
| 4,082,698 | 4/1978 | Shaw et al. | 252/469 |
| 4,289,654 | 9/1981 | Bertolini et al. | 502/312 |
| 4,290,920 | 9/1981 | Suresh et al. | 502/312 |
| 4,892,856 | 1/1990 | Kawajiri et al. | 502/247 |
| 5,493,052 | 2/1996 | Tenten et al. | 562/534 |
| 5,550,095 | 8/1996 | Naito et al. | 502/312 |

FOREIGN PATENT DOCUMENTS

| 0 668 102 | 8/1995 | European Pat. Off. |
| 0 668 103 | 8/1995 | European Pat. Off. |
| 0 711 745 | 5/1996 | European Pat. Off. |
| 43 02 991 | 8/1994 | Germany . |
| 52-153889 | of 1977 | Japan . |
| 52-23589 | of 1977 | Japan . |
| 58-166939 | of 1983 | Japan . |
| 3-218334 | of 1991 | Japan . |

Primary Examiner—Wayne Langel
Attorney, Agent, or Firm—Nields, Lemack & Dingman

[57] ABSTRACT

A catalyst having a high activity and mechanical strength and a process for preparing it are provided. The catalyst comprises molybdenum, vanadium, copper and antimony as essential components. The peak in X-ray diffractometry of the catalytically active component with Cu—Kα line is largest at 22.2±0.30° (2θ).

6 Claims, 2 Drawing Sheets

CATALYSTS AND PROCESS FOR THE PREPARATION THEREOF

BACKGROUND OF THE INVENTION

1. Field of the Invention

The present invention relates to a novel catalyst and a process for preparing it. More particularly, it relates to a catalyst suitable for use in the production of acrylic acid by catalytic oxidation of acrolein in gas phase with molecular oxygen, and to a process for preparing the catalyst.

1. Prior Art

Catalysts for producing acrylic acid by catalytic oxidation of acrolein in gas phase are described in Japanese Patent Publication Nos. 41-1775 (1966) and 44-12129 (1969).

Japanese Patent Application Laying Open No. 47-8360 (1972) describes a catalyst comprising antimony, molybdenum, vanadium and tungsten as essential components and a trace amount of copper. Further, Japanese Patent Application Laying Open No. 48-96514 (1973) discloses a catalyst comprising molybdenum, vanadium, tungsten and tin as essential components and optionally antimony and/or copper.

Japanese Patent Application Laying Open Nos. 51-11709 (1976), 52-23589 (1977), 52-153889 (1977), 58-166939 (1983) and 3-218334 (1991) disclose a catalyst comprising copper, tin, antimony and chromium as optional components; a catalyst containing an antimony-nickel compound; a coated catalyst containing copper and antimony as optional components; a ring catalyst containing copper and antimony as optional components; and a high-yield, high-productivity catalyst, respectively. Although some of these catalysts have been manufactured on a commercial scale and used in the production of acrylic acid, the productivity thereof is not always satisfactory. There has recently been an increasing need for a catalyst with a higher productivity as the demand for acrylic acid is increased.

In recent years, an increased amount of acrolein supplied per unit volume of a catalyst ("high load condition") has been used to improve the productivity in the production of acrylic acid by catalytic oxidation of acrolein in gas phase. Since the oxidizing reaction of acrolein is exothermic, hot spots are created due to increased heat accompanied with the increased amount of acrolein. These hot spots tend to cause entrainment of, for example, molybdenum which is most frequently used as the element constituting a catalytically active component.

If a catalyst used in this reaction is prepared by compression, extrusion or coating, and if the mechanical strength of the catalyst is low, powders of broken or peeled catalytically active component may clog a reaction vessel upon being filled with the catalyst, resulting in abnormal pressure rise of the reaction vessel. Therefore, it is desirable for a compressed, extruded or coated catalyst to have excellent mechanical strength such as attrition resistance.

SUMMARY OF THE INVENTION

The present inventors have made great efforts to provide a catalyst which meets the above mentioned requirements and found a catalyst having a higher activity at lower temperatures, a higher selectivity and higher mechanical strength (less attrition) as compared with conventional ones. Thus, the present invention has been attained.

Accordingly, the present invention provides:
(1) a catalyst in which a catalytically active component has a composition represented by the formula (1):

$$Mo_{12}V_aW_bCu_cSb_dX_eY_fZ_gO_h \quad (1)$$

wherein Mo, V, W, Cu, Sb and O represent molybdenum, vanadium, tungsten, copper, antimony and oxygen, respectively, X represents at least one element selected from the group consisting of alkali metals and thallium, Y represents at least one element selected from the group consisting of magnesium, calcium, strontium, barium and zinc, Z represents at least one element selected from the group consisting of niobium, cerium, tin, chromium, manganese, iron, cobalt, samarium, germanium, titanium and arsenic, a, b, c, d, e, f, g and h are atomic ratios of respective elements with $0<a\leq10$, $0<b\leq10$, $0<c\leq6$, $0<d\leq10$, $0\leq e\leq0.5$, $0\leq f\leq1$ and $0\leq g<6$, based on twelve (12) molybdenum atoms, and h is the number of oxygen atoms required to satisfy the total valence, wherein the strongest peak appears at 22.2±0.3° (2θ) in X-ray diffractometry of the catalytically active component with the copper Kα line where θ represents an angle of diffraction;

(2) a catalyst according to (1) above, which comprises a powder obtained by drying an aqueous solution or dispersion containing the metallic elements constituting the catalytically active component (hereinafter referred to as "catalytically active elements") or their compounds, and calcining the resulting dried powder, wherein an electric conductivity of a mixture of 5 g of said powder and 75 g of pure water ranges from 100 to 2,000 μS/cm as measured after stirring for 5 minutes;

(3) a catalyst according to (2) above, wherein the dried powder is obtained by spray drying;

(4) a catalyst according to (3) above, wherein the aqueous solution or dispersion containing the catalytically active elements or their compounds is obtained by mixing water and antimony trioxide as an antimony source;

(5) a catalyst obtained by compressing, extruding or coating a catalyst according to any one of (1) to (4) above, wherein the volumes of pores having a diameter in the range of from 0.01 to 0.1 μm, from 0.1 to 1 μm, from 1 to 10 μm, and from 10 to 200 μm are at most 20%, at most 30%, at least 40%, and at most 50%, respectively, based on the total volume of said pores having a diameter in the range of from 0.01 to 200 μm in the catalyst;

(6) a catalyst according to any one of (1) to (5) above for use in the production of acrylic acid by catalytically oxidizing acrolein in gas phase with molecular oxygen;

(7) a process for preparing a catalyst according to any one of (1) to (6) above, comprising the steps of
  (a) drying an aqueous solution or dispersion containing catalytically active elements or their compounds to provide a dried powder,
  (b) calcining the dried powder obtained in step (a) to produce a powder of a catalytically active component, and
  (c) coating a carrier with the powder of catalytically active component obtained in step (b), by using a tumble granulator;

(8) a process according to (7) above, wherein in step (c) a reinforcing material is used together with the powder of catalytically active component;

(9) a process according to (7) or (8) above, wherein in step (c) a binder is used together with the powder of catalytically active component;

(10) a process according to (9) above, wherein the binder is a diol or triol;

(11) a process according to (10) above, wherein the triol is glycerin; and

(12) a process according to (8) above, wherein the reinforcing material is a ceramic fiber.

Figure 1:
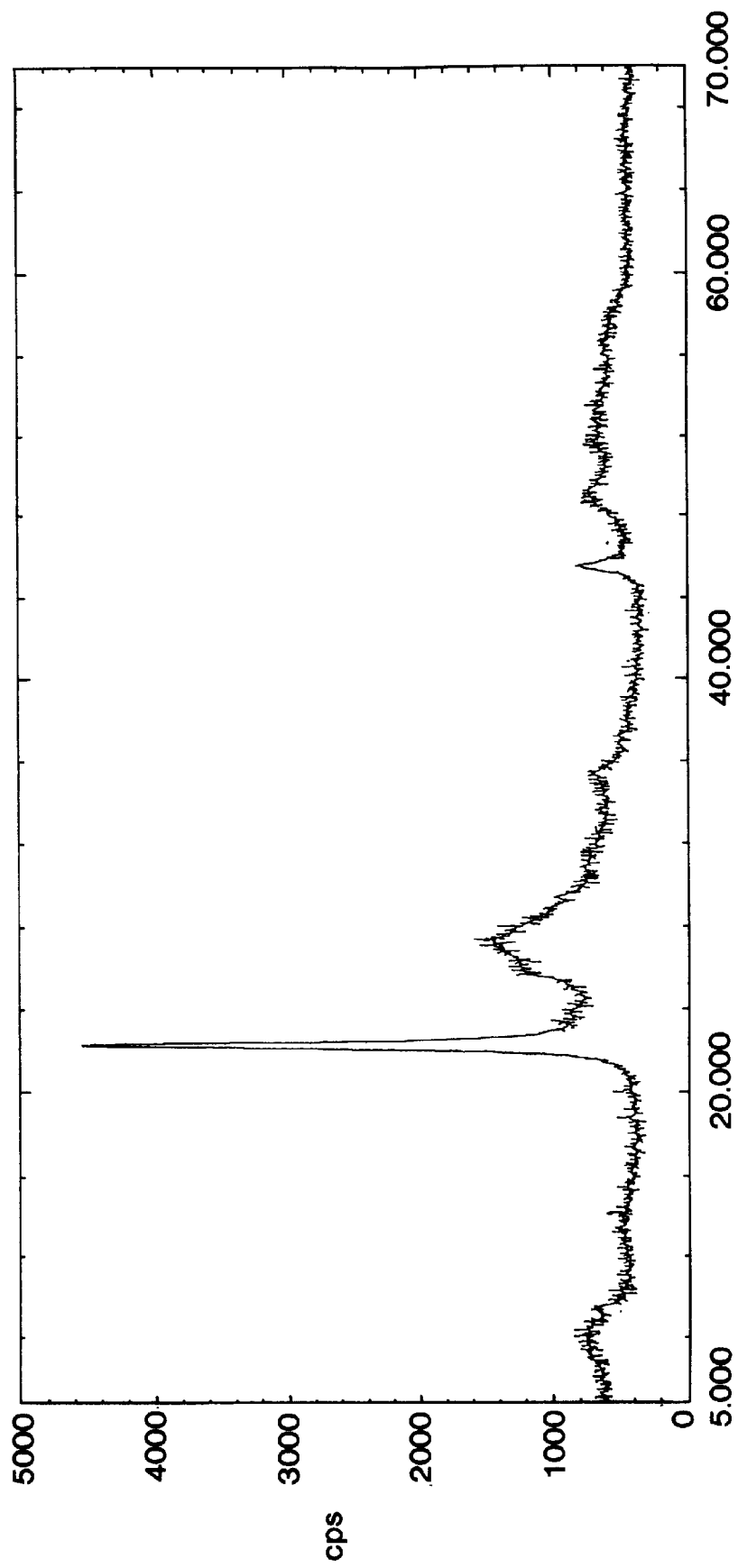
FIG. 1 shows the results of the X-ray diffractometry of the pre-calcined granule obtained in Example 1.

In the figures, the abscissa and ordinate represent 2θ and cps, respectively.

DESCRIPTION OF THE INVENTION

In the catalyst of the present invention, the atomic ratios of respective elements in the catalytically active component represented by the formula (1) are as aforementioned and are preferably $2 \leq a \leq 5$, $0.2 \leq b \leq 2$, $0.2 \leq c \leq 4$, $0.3 \leq d \leq 5$, $0 \leq e \leq 0.2$, $0 \leq f \leq 0.5$ and $0 \leq g \leq 3$.

The catalyst of the present invention may be prepared by drying an aqueous solution or dispersion containing the metallic elements constituting the catalytically active component or their compounds, calcining the resulting dried powder, and optionally shaping the calcined powder.

The compounds of the catalytically active elements used in the present invention are not particularly limited provided that they can be converted into oxides upon calcination, and may include chlorides, sulfates, nitrates, ammonium salts and oxides of the catalytically active elements. Illustrative examples of the compounds which may be used include molybdenum trioxide and molybdic acid or salts thereof as molybdenum compounds; vanadium pentaoxide, vanadyl sulfate and vanadic acid or salts thereof as vanadium compounds; tungstic acid or salts thereof as tungsten compounds; and copper oxide, copper sulfate, copper nitrate and copper molybdate as copper compounds. Illustrative examples of antimony compounds which may be used include antimony trioxide, antimony pentaoxide, antimony acetate and antimony trichloride. Among these antimony compounds, antimony trioxide is preferred and this is preferably used as it is without chemical treatment. This means that there is not used any chemical treatment for facilitating dissolution or dispersion of antimony trioxide in water, for example, by contacting it with an acid such as nitric or sulfuric acid, an oxidizing agent such as hydrogen peroxide, or an alkali. Antimony trioxide is preferably used in the form of fine powder.

The compounds of catalytically active elements may be used alone or as a mixture of two or more compounds.

In the preparation of the catalyst of the present invention, an aqueous solution or dispersion containing the catalytically active elements or their compounds is first prepared. This aqueous solution or dispersion is hereinafter referred simply as "slurry solution" unless otherwise specified. According to the present invention, the slurry solution is preferably an aqueous solution. The content of each catalytically active element or compound thereof in the slurry solution is not particularly limited so long as the atomic ratios of the respective catalytically active elements fall within the above specified ranges. The amount of water used is not particularly limited provided that all the elements and/or compounds can be completely dissolved or uniformly mixed. The amount of water may be suitably determined in view of the below mentioned drying step and temperature and usually is in the range of 200 to 2,000 parts by weight based on 100 parts of the total weight of the compounds. If the amount of water is too low, all the compounds can not be completely dissolved or uniformly mixed. Too much water may lead to problems of energy cost of the drying step or incomplete drying.

The uniformly mixed slurry solution is then dried. Methods for drying are not particularly limited so long as the slurry solution can be dried and a powdery product can be obtained, and may include for example drum, freeze and spray drying. Among these methods spray drying is preferred in the present invention since the slurry solution is dried to a powdery state in a short period of time. The drying temperature may depend upon the concentration and feed rate of the slurry solution and the temperature at the outlet of a dryer is generally 85 to 130° C. Preferably, the drying is carried out such that the resulting dried powder has an average particle size of 20 to 60 μm.

The catalyst of the present invention can be obtained by calcining the dried powder at 200 to 600° C. for 1 to 15 hours and optionally grinding the calcined powder, which is preferably shaped in a below mentioned manner. When the shaping step is carried out, the calcination may be preferably carried out in two steps, i.e., pre-calcination prior to the shaping step and post-calcination after the shaping step. The method for calcination may be any of known methods and is not particularly limited.

The process for preparing the catalyst employing the shaping step is carried out, for example, as mentioned below. The pre-calcination is generally carried out at a temperature of 250 to 500° C., preferably 300 to 450° C., for 1 to 15 hours, preferably 3 to 6 hours. The pre-calcination step prevents degradation and peeling of the catalytically active component when the finished shaped catalyst is filled in a reaction vessel; that is, a shaped catalyst with less attrition can be obtained.

The thus preliminarily calcined granule, hereinafter referred to as "pre-calcined granule" unless otherwise specified, is then shaped directly or optionally after grinding. If those pre-calcined granules or optionally ground powders which show an electric conductivity of 100 to 2,000 μS/cm, preferably 500 to 1,500 μS/cm, as measured in a mixture of 5 g of the granule or powder and 75 g of pure water after stirred at 0 to 15° C. for 5 minutes, are used, there is obtained a high performance catalyst with a very high activity and less attrition.

The catalyst which has high catalysis activity is obtained by the pre-calcination as mentioned before. Preferably, however, the pre-calcined granule is used after shaping. Upon shaping, the pre-calcined granule, optionally mixed with a binder, may be (A) compressed, (B) mixed with a shaping aid, such as silica gel, diatomaceous earth or alumina powder, and extruded into a spherical or ring shape, or (C) coated on a spherical carrier, such as silicon carbide, alumina, mullite or alundum, having a diameter of 2.5 to 10 mm by tumble granulation and so on.

The binder used may include water, ethanol, a high molecular weight binder such as polyvinyl alcohol, and an inorganic binder such as aqueous silica sol solution. Alcohols including diols, such as ethylene glycol, and triols, such as glycerin, are preferably used with glycerin being particularly preferred. The alcohols may be directly used but aqueous alcohol solutions having a concentration of 10% by weight or higher are effective to provide a high performance catalyst.

The amount of binder used is generally 10 to 50 parts by weight based on 100 parts by weight of the pre-calcined granule.

Optionally, a shaping aid, such as silica gel, diatomaceous earth or alumina powder, may also be used. The amount of shaping aid used is generally 5 to 60 parts by weight based on 100 parts by weight of the pre-calcined powder. Further, use of a reinforcing material, such as ceramic fiber or whisker, is useful to improve the mechanical strength of the catalyst. However, fibers such as potassium titanate whisker and basic magnesium carbonate whisker are not preferable since they are reactive with the catalytic component(s). The amount of fibers used is generally 1 to 30 parts by weight based on 100 parts by weight of the pre-calcined granule.

When used, the shaping aid and reinforcing material are generally mixed with the pre-calcined granule. The binder may be mixed with the pre-calcined granule, or may be added to a shaping machine prior to, simultaneously with or after the addition of the pre-calcined granule.

Among the shaping methods, the tumble granulation (C) is preferred as previously mentioned. Illustratively, into an apparatus having a stationary vessel and a planar or uneven disk provided in the bottom of the vessel, a carrier is added. The carrier is vigorously stirred due to repeated rotation and revolution when the disk is rotated at a high speed. A mixture of the binder, the pre-calcined granule, and the optional shaping aid and reinforcing material is added to coat the carrier with the mixture. The binder may be (1) preliminarily mixed with the mixture, (2) added into the stationary vessel simultaneously with the addition of the mixture, (3) added after the addition of the mixture, or (4) added prior to the addition of the mixture; or (5) both the binder and the mixture may be divided into two or more portions and the portions are added in any combined manner of (2) to (4) above. In the manner (5), it is preferred to use for example an autofeeder to adjust the addition rate so that, for example, any mixture does not adhere to the vessel wall or any mass composed of only the mixture is not formed.

Illustrative examples of the carriers which may be used in the method (C) include spherical carriers, such as silicon carbide, alumina, mullite and alundum, having a diameter of 2.5 to 10 mm. Among these carriers, those having a porosity of 30 to 50% and a water absorption of 10 to 30% are preferably used. The carrier is generally used in an amount such that the ratio of the pre-calcined granule to the total weight of the pre-calcined granule plus the carrier is 10 to 75% by weight, preferably 15 to 50% by weight.

The shaped product of the pre-calcined granule obtained by the the aforementioned method (A) to (C) may preferably have a diameter of 2 to 10 mm and a height of 3 to 20 mm in the case of a cylindrical shape or a diameter of 3 to 15 mm in the case of a spherical shape.

The catalyst may be obtained by post-calcining the shaped product of the pre-calcined granule. The post-calcination is generally carried out at a temperature of 250 to 500° C., preferably 300 to 450° C., for 1 to 50 hours. According to the present invention, the shaped product obtained by post-calcination (hereinafter referred to as "shaped catalyst") shows the strongest peak at 22.2±0.3° (2θ) in X-ray diffractometry with Cu—Kα line of the catalytically active component, and the intensity of this strongest peak is at least identical with, preferably at least 1.6 times, more preferably at least 2 times, most preferably at least 4 times, the intensity of any other peak. The symbol 2θ herein means a double value of an angle of diffraction (θ) in the X-ray diffractometry. The other peaks appear at values of 2θ other than 22.2±0.3° and may include peaks originating from molybdenum oxide as described in for example ASTM (American Society for Testing Material) cards 5-508, 21-569, 35-609 and 37-1445, as well as peaks originating from compounds in which molybdenum oxide is partially substituted with at least one of the catalytically active elements of the present invention, such as vanadium, tungsten and antimony, and compounds of the catalytically active elements used as starting materials. In the X-ray diffractometry of a shaped catalyst, the strongest peak may sometimes originate from alumina used as a carrier or an optional reinforcing material. These peaks are not taken into consideration in the present invention. In order to obtain a shaped catalyst having such a specific X-ray diffraction pattern as above mentioned, it is preferable to use a pre-calcined granule which shows same characteristics with those obtained after post-calcination in the X-ray diffractometry in the same manner.

In the shaped catalyst according to the present invention, it is preferred that the total volume of pores having a diameter of 0.01 to 200 μm is 0.01 to 1.0 ml/g, preferably 0.01 to 0.4 ml/g, and the specific surface area is 0.5 to 10 $m^2/g$, preferably 1.0 to 5.0 $m^2/g$. The pore distribution is preferably such that the volumes of pores having a diameter in the range of from 0.01 to 0.1 μm, from 0.1 to 1 μm, from 1 to 10 μm, and from 10 to 200 μm are at most 20%, at most 30%, at least 40%, and at most 50%, respectively, based on the total volume of said pores having a diameter in the range of from 0.01 to 200 μm in the catalyst.

The catalyst of the present invention has a higher activity at lower temperatures and a higher selectivity of acrylic acid as compared with conventional ones and, therefore, can be used in the reaction under high load conditions. Further, the catalyst has excellent attrition resistance and a very great commercial value.

EXAMPLES

The present invention will be described in more detail by way of the following examples and comparative examples. However, the present invention is not limited to the following examples unless departing from the scope thereof as defined in the attached claims.

In the following examples and comparative examples, all parts are by weight and the acrolein conversion (% by mole), acrylic acid selectivity (% by mole) and acrylic acid yield (%) are defined by the following equations (2) to (4), respectively:
(2) Acrolein conversion (mole %)=100×(acrolein reacted in mole)/(acrolein supplied in mole)
(3) Acrylic acid selectivity (mole %)=100×(acrylic acid produced in mole)/(acrolein converted in mole)
(4) Acrylic acid yield (%)=100×(acrylic acid produced in mole)/(acrolein supplied in mole)

The X-ray diffraction was measured by using JDX-7F from JEOL LTD. or RINT-1100V from RIGAKU.

The pore distribution was measured by using a mercury porosimeter Poresizer 9320 from MICROMERITICS.

The attrition resistance was measured by an attrition resistance tester from KAYAGAKI IRIKA KOGYO. A catalyst sample was rotated at 25 rpm for 10 minutes and passed through a 2.36 mm standard sieve. The weight of catalyst remaining on the sieve was measured and the attrition resistance (% by weight) was determined by the following equation (5):
(5) Attrition resistance (wt %)=100×(sample weight−weight of residual catalyst on 2.36 mm sieve)/(sample weight)

The electric conductivity was determined by dispersing 5 g of a sample in 75 g of pure water, stirring for 5 minutes, and measuring the conductivity by CM-20S from TOA Electronics Ltd.

Example 1

To a formulating tank (A) equipped with a stirring motor, 600 parts of deionized water at 95° C. and 16.26 parts of ammonium tungstate were added and stirred. Then, 18.22 parts of ammonium metavanadate and 110 parts of ammonium molybdate were dissolved. Further, 3.78 parts of antimony trioxide powder were added. Into a formulating tank (B) containing 96 parts of deionized water, 15.56 parts of copper sulfate were dissolved and the resulting solution was added to the formulating tank (A) to form a slurry solution. The slurry solution was dried in a spray drier while adjusting the feed rate such that the temperature at the outlet of the drier was about 100° C. The resulting granule was placed in a furnace at room temperature and the temperature of the furnace was raised at a rate of about 60° C. per hour. Then, the granule was pre-calcined at 390° C. for about 5 hours. The 2θ values in the X-ray diffractometry of the pre-calcined granule were measured and a main peak at 22.2° and a second largest peak at 27.0° were observed where the intensity ratio was 100:23. The results of measurement of the 2θ values in the X-ray diffractometry are shown in FIG. 1.

The pre-calcined granule was ground in a ball mill to yield a powder (hereinafter referred to as "pre-calcined powder"). The pre-calcined powder had an electric conductivity of 1050 μS/cm. In a tumble granulator, 12 parts of the pre-calcined powder were applied on 36 parts of alundum carrier with a porosity of 40%, a water absorption of 19.8% and a diameter of 4 mm while sprinkling 2.4 parts of an aqueous 20% by weight solution of glycerin on the carrier. The thus shaped product was placed in a furnace at room temperature and the temperature of the furnace was raised at a rate of about 70° C. per hour. Then, the product was calcined (post-calcination) at 390° C. for 5 hours to yield a catalyst of the present invention. The catalytically active component except oxygen in the catalyst of the present invention had the following composition in elementary ratio:

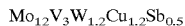

$Mo_{12}V_3W_{1.2}Cu_{1.2}Sb_{0.5}$

Figure 2:
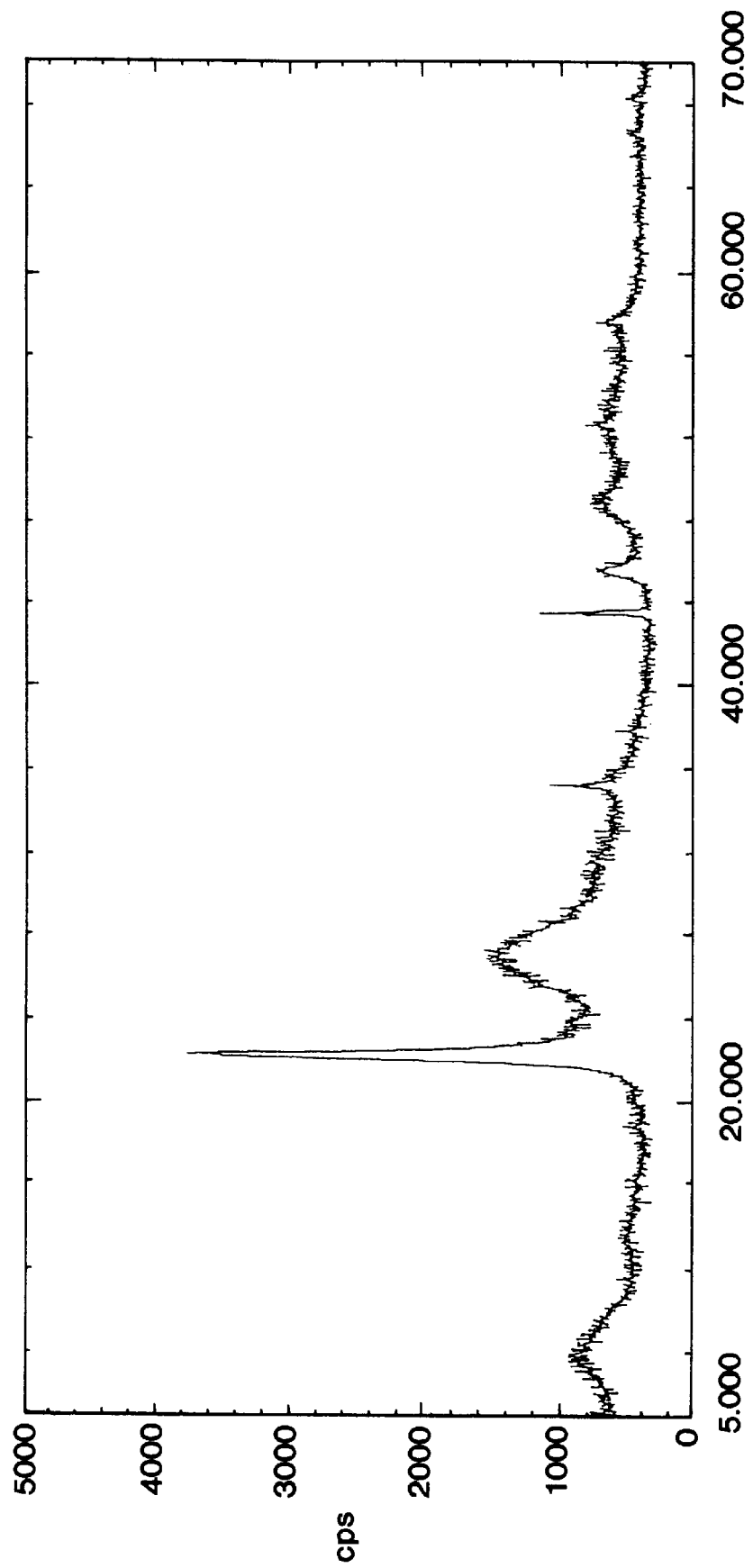
FIG. 2 shows the results of the X-ray diffractometry of the catalyst obtained in Example 1.

The X-ray diffractometry was carried out on the catalyst. A peak originating from the alundum carrier was observed but the other peaks were substantially identical with those observed on the pre-calcined granule. The results of measurement of the 2θ values in the X-ray diffractometry are shown in FIG. 2.

The pore distribution of the catalyst was measured. The volumes of pores having a diameter in the range of from 0.01 to 0.1 μm, from 0.1 to 1 μm, from 1 to 10 μm, and from 10 to 200 μm were 7%, 7%, 64%, and 22%, respectively, based on the total volume of said pores having a diameter in the range of from 0.01 to 200 μm in the catalyst, which was 0.09 ml/g.

The catalyst had an attrition resistance of 0.3% by weight and a specific surface area of 2.2 m²/g.

Into a reaction vessel with an inner diameter of 21.4 mm, 30 ml of the catalyst were filled and a gaseous reaction mixture was supplied at SV [space velocity=(the volume of gas per unit time)/(the volume of the filled catalyst)] of 1800 per hour. The reaction mixture was obtained from catalytic oxidation of propylene in gas phase using a molybdenum-bismuth catalyst and supplemented with oxygen and nitrogen. The mixture had the following composition:

| | |
|---|---|
| Acrolein | 5.5% by volume |
| Unreacted propylene and other organic compounds | 1.3% by volume |
| Oxygen | 7.4% by volume |
| Steam | 27.0% by volume |
| Inert gas including nitrogen | 58.8% by volume |

The results of the reaction are given in Table 1.

Example 2

In a tumble granulator, 24 parts of the pre-calcined powder obtained in Example 1 were applied on 36 parts of alundum carrier with a porosity of 34%, a water absorption of 17% and a diameter of 3.5 mm while sprinkling 3 parts of an aqueous 20% by weight solution of glycerin on the carrier. The thus shaped product was placed in a furnace at room temperature and the temperature of the furnace was raised at a rate of about 70° C. per hour. Then, the product was calcined at 390° C. for 5 hours to yield a catalyst of the present invention. The catalytically active component except oxygen in the catalyst of the present invention had the following composition in elementary ratio:

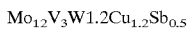

$Mo_{12}V_3W_{1.2}Cu_{1.2}Sb_{0.5}$

The pore distribution of the catalyst was measured. The volumes of pores having a diameter in the range of from 0.01 to 0.1 μm, from 0.1 to 1 μm, from 1 to 10 μm, and from 10 to 200 μm were 10%, 9%, 63%, and 18%, respectively, based on the total volume of said pores having a diameter in the range of from 0.01 to 200 μm in the catalyst. The catalyst had an attrition resistance of 0.5% by weight and a specific surface area of 3.5 m²/g.

The catalyst was subjected to the reaction as in Example 1. The results thereof are given in Table 1.

Examples 3 to 6

The procedures of Example 1 were repeated except that in Examples 3 to 6, 5.19 parts, 10.37 parts, 23.33 parts and 32.40 parts, respectively, of copper sulfate were used. The catalytically active components except oxygen in the catalysts of the present invention had the following compositions in elementary ratio:

| | |
|---|---|
| Example 3 | $Mo_{12}V_3W_{1.2}Cu_{0.4}Sb_{0.5}$ |
| Example 4 | $Mo_{12}V_3W_{1.2}Cu_{0.8}Sb_{0.5}$ |
| Example 5 | $Mo_{12}V_3W_{1.2}Cu_{1.8}Sb_{0.5}$ |
| Example 6 | $Mo_{12}V_3W_{1.2}Cu_{2.5}Sb_{0.5}$ |

The X-ray diffractometry was carried out on the catalytically active components of the catalysts and the values of 2θ were measured. In each catalyst, a main peak was observed at 22.2° which is characteristic of the present invention. However, the intrinsic peaks of molybdenum oxide were very broad and overlapped with each other; thus, no sharp peak was observed. The pre-calcined powders used in these Examples had an electric conductivity in the range of 200 to 1400 μS/cm. The catalysts had an attrition resistance of 0.5% or lower.

The catalysts were subjected to the reaction as in Example 1. The results thereof are given in Table 1.

TABLE 1

| Example | 1 | 2 | 3 | 4 | 5 | 6 |
|---|---|---|---|---|---|---|
| Reaction temperature (° C.) | 250 | 230 | 255 | 250 | 255 | 260 |
| Acrolein conversion (mole %) | 99.1 | 98.7 | 99.0 | 98.9 | 99.1 | 99.0 |
| Acrylic acid selectivity (mole %) | 98.5 | 98.2 | 98.2 | 98.4 | 98.0 | 98.3 |
| Acrylic acid yield (mole %) | 97.6 | 96.9 | 97.2 | 97.3 | 97.1 | 97.3 |

Examples 7 to 10

The procedures of Example 1 were repeated except that in Examples 7 to 10, 2.27 parts, 7.56 parts, 15.13 parts and 22.70 parts, respectively, of antimony trioxide were used.

The catalytically active components except oxygen in the catalysts of the present invention had the following compositions in elementary ratio:

| | |
|---|---|
| Example 7 | $Mo_{12}V_3W_{1.2}Cu_{1.2}Sb_{0.3}$ |
| Example 8 | $Mo_{12}V_3W_{1.2}Cu_{1.2}Sb_{1.0}$ |
| Example 9 | $Mo_{12}V_3W_{1.2}Cu_{1.2}Sb_{2.0}$ |
| Example 10 | $Mo_{12}V_3W_{1.2}Cu_{1.2}Sb_{3.0}$ |

The X-ray diffractometry was carried out on the catalytically active components of the catalysts and the values of 2θ were measured. In each catalyst, a main peak was observed at 22.2° which is characteristic of the present invention. However, the intrinsic peaks of molybdenum oxide were very broad and overlapped with each other; thus, no sharp peak was observed. The pre-calcined powders used in these Examples had an electric conductivity in the range of 150 to 1200 μS/cm. The catalysts had an attrition resistance of 0.6% or lower.

The catalysts were subjected to the reaction as in Example 1. The results thereof are given in Table 2.

Example 11

To a formulating tank (A) equipped with a stirring motor, 600 parts of deionized water at 95° C. and 16.26 parts of ammonium tungstate were added and stirred. Then, 18.22 parts of ammonium metavanadate and 110 parts of ammonium molybdate were dissolved. Further, 3.78 parts of antimony trioxide powder were added. Into a formulating tank (B) containing 96 parts of deionized water, 15.56 parts of copper sulfate and 1.05 parts of potassium nitrate were dissolved and the resulting solution was added to the formulating tank (A) to form a slurry solution.

The slurry solution was dried in a spray drier while adjusting the feed rate such that the temperature at the outlet of the drier was about 100° C. The resulting granule was placed in a furnace at room temperature and the temperature of the furnace was raised at a rate of about 60° C. per hour. Then, the granule was pre-calcined at 390° C. for about 5 hours to yield a pre-calcined granule.

In a tumble granulator, 12 parts of a pre-calcined powder obtained by grinding the pre-calcined granule in a ball mill were applied on 36 parts of alundum carrier with a diameter of 4 mm while sprinkling 2.4 parts of an aqueous 20% by weight solution of glycerin on the carrier. The thus shaped product was placed in a furnace at room temperature and the temperature of the furnace was raised at a rate of about 70° C. per hour. Then, the product was calcined at 390° C. for 5 hours to yield a catalyst of the present invention. The catalytically active component except oxygen in the catalyst had the following composition in elementary ratio:

$Mo_{12}V_3W1.2Cu_{1.2}Sb_{0.5}K_{0.2}$

The 2θ values in the X-ray diffractometry of the pre-calcined granule used were measured and a main peak at 22.2° and a second largest peak at 26.70 were observed where the intensity ratio was 100:28. Similar results were observed for the catalytically active component of the catalyst.

The pore distribution of the catalyst was measured. The volumes of pores having a diameter in the range of from 0.01 to 0.1 μm, from 0.1 to 1 μm, from 1 to 10 μm, and from 10 to 200 μm were 9%, 6%, 73%, and 12%, respectively, based on the total volume of said pores having a diameter in the range of from 0.01 to 200 μm in the catalyst. The catalyst had an attrition resistance of 0.3% by weight and a specific surface area of 1.8 m²/g.

The catalyst was subjected to the reaction as in Example 1. The results thereof are given in Table 2.

Example 12

The procedures of Example 11 were repeated except that 2.45 parts of calcium nitrate were substituted for potassium nitrate. The catalytically active component except oxygen in the catalyst of the present invention had the following composition in elementary ratio:

$Mo_{12}V_3W1.2Cu_{1.2}Sb_{0.5}Ca_{0.2}$

The 2θ values in the X-ray diffractometry of the pre-calcined granule used were measured and a main peak at 22.2° and a second largest peak at 27.3° were observed where the intensity ratio was 100:36. Similar results were observed for the catalytically active component of the catalyst of the present invention.

The catalyst was subjected to the reaction as in Example 1. The results thereof are given in Table 2.

Example 13

To a formulating tank (A) equipped with a stirring motor, 600 parts of deionized water at 95° C. and 16.26 parts of ammonium tungstate were added and stirred. Then, 18.22 parts of ammonium metavanadate and 110 parts of ammonium molybdate were dissolved. Further, 3.78 parts of antimony trioxide powder were added. After 20 minutes, 4.47 parts of cerium oxide were added. Into a formulating tank (B) containing 96 parts of deionized water, 15.05 parts of copper nitrate were dissolved and the resulting solution was added to the formulating tank (A) to form a slurry solution.

The slurry solution was dried in a spray drier while adjusting the feed rate such that the temperature at the outlet of the drier was about 100° C. The resulting granule was placed in a furnace at room temperature and the temperature of the furnace was raised at a rate of about 60° C. per hour. Then, the granule was pre-calcined at 370° C. for about 5 hours to yield a pre-calcined granule.

In a tumble granulator, 12 parts of a pre-calcined powder obtained by grinding the pre-calcined granule in a ball mill were applied on 36 parts of alundum carrier with a diameter of 4 mm while sprinkling 2.4 parts of an aqueous 20% by weight solution of glycerin on the carrier. The thus shaped product was placed in a furnace at room temperature and the temperature of the furnace was raised at a rate of about 70° C. per hour. Then, the product was calcined at 370° C. for 5 hours to yield a catalyst of the present invention. The catalytically active component except oxygen in the catalyst had the following composition in elementary ratio:

$Mo_{12}V_3W_{1.2}Cu_{1.2}Sb_{0.5}Ce_{0.5}$

The 2θ values in the X-ray diffractometry of the pre-calcined granule used were measured and a main peak at 22.2° and a second largest peak at 28.5° were observed where the intensity ratio was 100:34. Similar results were observed for the catalytically active component of the catalyst.

The pore distribution of the catalyst was measured. The volumes of pores having a diameter in the range of from 0.01 to 0.1 μm, from 0.1 to 1 μm, from 1 to 10 μm, and from 10 to 200 μm were 13%, 6%, 69%, and 12%, respectively, based on the total volume of said pores having a diameter in the range of from 0.01 to 200 μm in the catalyst. The catalyst had an attrition resistance of 0.3% by weight and a specific surface area of 2.0 m²/g.

The catalyst was subjected to the reaction as in Example 1. The results thereof are given in Table 2.

TABLE 2

| Example | 7 | 8 | 9 | 10 | 11 | 12 | 13 |
|---|---|---|---|---|---|---|---|
| Reaction temperature (° C.) | 255 | 250 | 260 | 265 | 250 | 255 | 250 |
| Acrolein conversion (mole %) | 98.6 | 99.0 | 98.7 | 99.1 | 98.5 | 98.3 | 98.8 |
| Acrylic acid selectivity (mole %) | 98.9 | 98.1 | 98.0 | 97.0 | 97.7 | 96.4 | 97.2 |
| Acrylic acid yield (mole %) | 97.5 | 97.1 | 96.7 | 96.1 | 96.2 | 94.8 | 96.0 |

Example 14

The procedures of Example 13 were repeated except that 3.45 parts of niobium oxide were substituted for cerium oxide. The catalytically active component except oxygen in the catalyst of the present invention had the following composition in elementary ratio:

$$Mo_{12}V_3W_{1.2}Cu_{1.2}Sb_{0.5}Nb_{0.5}$$

The 2θ values in the X-ray diffractometry of the pre-calcined granule used were measured and a main peak at 22.2° and a second largest peak at 22.6° were observed where the intensity ratio was 100:33. A small peak of niobium oxide was also observed. Similar results were observed for the catalytically active component of the catalyst of the present invention.

The catalyst was subjected to the reaction as in Example 1. The results thereof are given in Table 3.

Example 15

To a formulating tank (A) equipped with a stirring motor, 600 parts of deionized water at 95° C. and 16.26 parts of ammonium tungstate were added and stirred. Then, 18.22 parts of ammonium metavanadate and 110 parts of ammonium molybdate were dissolved. Further, 3.78 parts of antimony trioxide powder were added. Into a formulating tank (B) containing 96 parts of deionized water, 15.56 parts of copper sulfate, 0.52 parts of potassium nitrate and 2.66 parts of magnesium nitrate were dissolved and the resulting solution was added to the formulating tank (A) to form a slurry solution.

Subsequently, the procedures of Example 11 were repeated to yield a catalyst of the present invention. The catalytically active component except oxygen in the catalyst had the following composition in elementary ratio:

$$Mo_{12}V_3W_{1.2}Cu_{1.2}Sb_{0.5}K_{0.1}Mg_{0.2}$$

The 2θ values in the X-ray diffractometry of the pre-calcined granule used were measured and a main peak at 22.2° and a second largest peak at 27.3° were observed where the intensity ratio was 100:41. Similar results were observed for the catalytically active component of the catalyst.

The pore distribution of the catalyst was measured. The volumes of pores having a diameter in the range of from 0.01 to 0.1 μm, from 0.1 to 1 μm, from 1 to 10 μm, and from 10 to 200 μm were 7%, 5%, 80%, and 8%, respectively, based on the total volume of said pores having a diameter in the range of from 0.01 to 200 μm in the catalyst. The catalyst had an attrition resistance of 0.6% by weight and a specific surface area of 1.5 m²/g.

The catalyst was subjected to the reaction as in Example 1. The results thereof are given in Table 3.

Example 16

To a formulating tank (A) equipped with a stirring motor, 600 parts of deionized water at 95° C. and 16.26 parts of ammonium tungstate were added and stirred. Then, 18.22 parts of ammonium metavanadate and 110 parts of ammonium molybdate were dissolved. Further, 3.78 parts of antimony trioxide powder were added. After 20 minutes, 1.56 parts of tin oxide were added. Into a formulating tank (B) containing 96 parts of deionized water, 15.56 parts of copper sulfate, 0.22 parts of sodium nitrate and 1.10 parts of strontium nitrate were dissolved and the resulting solution was added to the formulating tank (A) to form a slurry solution.

Subsequently, the procedures of Example 11 were repeated to yield a catalyst of the present invention. The catalytically active component except oxygen in the catalyst had the following composition in elementary ratio:

$$Mo_{12}V_3W_{1.2}Cu_{1.2}Sb_{0.5}Na_{0.05}Sr_{0.1}Sn_{0.2}$$

The 2θ values in the X-ray diffractometry of the pre-calcined granule used were measured and a peak was observed at 22.2° which is characteristic of the present invention. However, the intrinsic peaks of molybdenum oxide at 23 to 29° were scarcely observed. Similar results were observed for the catalytically active component of the catalyst.

The catalyst was subjected to the reaction as in Example 1. The results thereof are given in Table 3.

Examples 17 and 18

The procedures of Example 1 were repeated except that in Examples 17 and 18, 12.15 parts and 24.30 parts, respectively, of ammonium metavanadate were used. The catalytically active components except oxygen in the catalysts of the present invention had the following compositions in elementary ratio:

| Example 17 | $Mo_{12}V_2W_{1.2}Cu_{1.2}Sb_{0.5}$ |
| Example 18 | $Mo_{12}V_4W_{1.2}Cu_{1.2}Sb_{0.5}$ |

The 2θ values in the X-ray diffractometry of the pre-calcined ) granules used were measured. In each catalyst, a peak was observed at 22.2° which is characteristic of the present invention. However, the intrinsic peaks of molybdenum oxide at 23 to 29° were scarcely observed. Similar results were also observed for the catalytically active components of the catalysts.

The catalysts were subjected to the reaction as in Example 1. The results thereof are given in Table 3.

Examples 19 and 20

The procedures of Example 1 were repeated except that in Examples 19 and 20, 6.78 parts and 27.11 parts, respectively, of ammonium tungstate were used. The catalytically active components except oxygen in the catalysts of the present invention had the following compositions in elementary ratio:

| Example 19 | $Mo_{12}V_3W_{0.5}Cu_{1.2}Sb_{0.5}$ |
| Example 20 | $Mo_{12}V_3W_{2.0}Cu_{1.2}Sb_{0.5}$ |

The 2θ values in the X-ray diffractometry of the pre-calcined granules used were measured. In the catalyst of Example 19, a peak was observed at 22.1° which is characteristic of the present invention while no intrinsic peaks of molybdenum oxide were observed. Similarly, a peak was observed at 22.2° which is characteristic of the present invention while no intrinsic peaks of molybdenum oxide were observed in the catalyst of Example 20. Similar results were also observed for the catalytically active components of the catalysts.

The catalysts were subjected to the reaction as in Example 1. The results thereof are given in Table 3.

TABLE 3

| Example | 14 | 15 | 16 | 17 | 18 | 19 | 20 |
|---|---|---|---|---|---|---|---|
| Reaction temperature (° C.) | 255 | 260 | 260 | 255 | 250 | 250 | 260 |
| Acrolein conversion (mole %) | 98.6 | 98.6 | 97.8 | 99.1 | 98.5 | 98.5 | 98.7 |
| Acrylic acid selectivity (mole %) | 96.8 | 98.7 | 98.3 | 97.3 | 98.4 | 98.2 | 96.7 |
| Acrylic acid yield (mole %) | 95.4 | 97.3 | 96.1 | 96.4 | 96.9 | 96.7 | 95.4 |

Example 21

The procedures of Example 1 were repeated except that the shaped product obtained in Example 1 was calcined at 440° C. for about 2.5 hours. The catalytically active component except oxygen in the catalyst of the present invention had the following composition in elementary ratio:

$Mo_{12}V_3W_{1.2}Sb_{0.5}Cu_{1.2}$

The 2θ values in the X-ray diffractometry of the catalytically active component in the catalyst were measured and a main peak at 22.2° and a second largest peak at 23.3° were observed where the intensity ratio was 100:41. The catalyst had an attrition resistance of 0.4% by weight.

The catalyst was subjected to the reaction as in Example 1. The results thereof are given in Table 4.

Example 22

The procedures of Example 1 were repeated except that the shaped product obtained in Example 1 was calcined at 480° C. for about 1 hour. The catalytically active component except oxygen in the catalyst of the present invention had the following composition in elementary ratio:

$Mo_{12}V_3W_{1.2}Cu_{1.2}Sb_{0.5}$

The 2θ values in the X-ray diffractometry of the catalytically active component in the catalyst were measured and a main peak at 22.2° and a second largest peak at 23.0° were observed where the intensity ratio was 100:60. The catalyst had an attrition resistance of 0.3% by weight. The catalyst was subjected to the reaction as in Example 1. The results thereof are given in Table 4.

Example 23

The procedures of Example 1 were repeated except that the pre-calcined powder obtained in Example 1 was shaped using an aqueous 30% by weight solution of ethylene glycol as a binder. The catalyst was subjected to X-ray diffractometry. Although some peaks of alumina based on the alundum carrier were detected, other peaks were similar to those observed for the pre-calcined granule.

The pore distribution of the catalyst was measured. The volumes of pores having a diameter in the range of from 0.01 to 0.1 μm, from 0.1 to 1 μm, from 1 to 10 μm, and from 10 to 200 μm were 11%, 10%, 67%, and 12%, respectively, based on the total volume of said pores having a diameter in the range of from 0.01 to 200 μm in the catalyst. The catalyst had an attrition resistance of 0.6% by weight and a specific surface area of 2.2 m²/g. The catalyst was subjected to the reaction as in Example 1. The results thereof are given in Table 4.

Example 24

Twenty-four (24) parts of the pre-calcined powder obtained in Example 1 were mixed with 1.2 parts of silica-alumina fiber with an average fiber length of 100 μm and an average fiber diameter of 2.0 μm to form a mixture. In a tumble granulator, 34.8 parts of alundum carrier with a porosity of 34%, a water absorption of 17% and a diameter of 3.5 mm were coated with the mixture while sprinkling 3 parts of an aqueous 20% by weight solution of glycerin on the carrier. While raising the temperature of the furnace from room temperature at a rate of about 70° C. per hour, calcination was carried out at 390° C. for 2.5 hours to yield a catalyst. The pore distribution of the catalyst was measured. The volumes of pores having a diameter in the range of from 0.1 to 1 μm, from 1 to 10 μm, and from 10 to 200 μm were 11%, 72%, and 17%, respectively, based on the total volume of said pores having a diameter in the range of from 0.01 to 200 μm in the catalyst. The catalyst had an attrition resistance of 0.1% by weight.

The catalyst was subjected to the reaction as in Example 1. The results thereof are given in Table 4.

Example 25

The procedures of Example 24 were repeated except that 23 parts of a mixture of 22 parts of the pre-calcined powder obtained in Example 1 with 1 part of silicon carbide whisker, 5 parts of an aqueous 20% by weight glycerin solution and 66 parts of alundum carrier with a porosity of 34%, a water absorption of 17% and a diameter of 3.5 mm were used to yield a catalyst of the present invention.

The pore distribution of the catalyst was measured. The volumes of pores having a diameter in the range of from 0.1 to 1 μm, from 1 to 10 μm, and from 10 to 200 μm were 15%, 73%, and 12%, respectively, based on the total volume of said pores having a diameter in the range of from 0.01 to 200 μm in the catalyst. The catalyst had an attrition resistance of 0.2% by weight.

The catalyst was subjected to the reaction as in Example 1. The results thereof are given in Table 4.

TABLE 4

| Example | 21 | 22 | 23 | 24 | 25 |
|---|---|---|---|---|---|
| Reaction temperature (° C.) | 255 | 270 | 265 | 225 | 245 |
| Acrolein conversion (mole %) | 99.3 | 98.3 | 98.7 | 99.3 | 98.9 |
| Acrylic acid selectivity (mole %) | 98.1 | 98.6 | 97.6 | 98.0 | 98.1 |

TABLE 4-continued

| Example | 21 | 22 | 23 | 24 | 25 |
|---|---|---|---|---|---|
| Acrylic acid yield (mole %) | 97.4 | 96.9 | 96.3 | 97.3 | 97.0 |

Comparative Example 1

The procedures of Example 1 were repeated except that no antimony trioxide was used to yield a catalyst. The catalytically active component except oxygen in the catalyst of the present invention had the following composition in elementary ratio:

$$Mo_{12}V_3W_{1.2}Cu_{1.2}$$

The catalyst was subjected to the reaction as in Example 1. The results thereof are given in Table 5.

Comparative Example 2

The procedures of Example 1 were repeated except that no copper oxide was used to yield a catalyst. The catalytically active component except oxygen in the catalyst of the present invention had the following composition in elementary ratio:

$$Mo_{12}V_3W_{1.2}Sb_{0.5}$$

The catalyst was subjected to the reaction as in Example 1. The results thereof are given in Table 5.

TABLE 5

| Comparative Example | 1 | 2 |
|---|---|---|
| Reaction temperature (° C.) | 280 | 300 |
| Acrolein conversion (mole %) | 98.0 | 96.8 |
| Acrylic acid selectivity (mole %) | 95.0 | 89.3 |
| Acrylic acid yield (mole %) | 93.5 | 86.4 |

As seen from the above results, the catalyst of the present invention shows a high reaction activity at temperatures about 10 to 70° C. lower than conventional catalysts.

What is claimed is:

1. A process for preparing a catalyst whose catalytically active component has a composition represented by the formula (1):

$$Mo_{12}V_aW_bCu_cSb_dX_eY_fZ_gO_h \quad (1)$$

wherein Mo, V, W, Cu, Sb and O represent molybdenum, vanadium, tungsten, copper, antimony and oxygen, respectively, X represents at least one element selected from the group consisting of alkali metals and thallium, Y represents at least one element selected from the group consisting of magnesium, calcium, strontium, barium and zinc, Z represents at least one element selected from the group consisting of niobium, cerium, tin, chromium, manganese, iron, cobalt, samarium, germanium, titanium and arsenic, a, b, c, d, e, f, g and h are atomic ratios of respective elements with $0<a\leq10$, $0.2\leq b\leq10$, $0<c\leq6$, $0<d\leq10$, $0\leq e\leq0.5$, $0\leq f\leq1$ and $0\leq g<6$, based on twelve (12) molybdenum atoms, and h is the number of oxygen atoms required to satisfy the total valence, wherein the strongest peak appears at 22.2±0.3° (2θ) in X-ray diffractometry of the catalytically active component with the copper Kα line where θ represents an angle of diffraction and the intensity of the peak is at least 1.6 times that of any other peak, which process comprises the step of spray-drying an aqueous solution or dispersion containing the metallic elements constituting the catalytically active components or their compounds to provide a dried powder wherein antimony trioxide is used as an antimony source and is not subjected to any chemical treatment in the aqueous solution or dispersion.

2. The process of claim 1, further comprising the step of calcining the resulting dried powder.

3. A catalyst obtained by the process of claim 1 or 2.

4. A catalyst obtained by the process of claim 2, wherein the electric conductivity of a mixture of 5 g of the dried, calcined powder and 75 g of pure water range from 100 to 2,000 μS/cm as measured after stirring for 5 minutes.

5. A shaped catalyst obtained by compressing, extruding or coating a catalyst of claim 3, wherein the volumes of pores having a diameter in the range of from 0.01 to 0.1 μm, from 0.1 to 1 μm, from 1 to 10 μm, and from 10 to 200 μm are at most 20%, at most 30%, at least 40% and at most 50%, respectively, based on the total volume of said pores having a diameter in the range of from 0.01 to 200 μm in the catalyst.

6. A process for the production of acrylic acid, comprising catalytically oxidizing acrolein in the gas phase with molecular oxygen in the presence of the catalyst of claim 3.

* * * * *